(12) United States Patent
Kassebaum

(10) Patent No.: US 6,500,782 B1
(45) Date of Patent: *Dec. 31, 2002

(54) HERBICIDAL COMPOSITIONS AND METHODS FOR PREPARING AND USING THE SAME

(75) Inventor: James W. Kassebaum, Indianapolis, IN (US)

(73) Assignee: Monsanto Technology LLC, St. Louis, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/570,367

(22) Filed: Dec. 11, 1995

Related U.S. Application Data

(63) Continuation of application No. 07/739,945, filed on Aug. 2, 1991, now abandoned.

(51) Int. Cl.[7] .......................... A01N 25/30; A01N 57/02
(52) U.S. Cl. ........................................ 504/206; 504/363
(58) Field of Search .................................. 504/116, 206, 504/363

(56) References Cited

U.S. PATENT DOCUMENTS

| | | | | |
|---|---|---|---|---|
| 3,799,758 A | * | 3/1974 | Franz | 71/86 |
| 3,938,986 A | * | 2/1976 | Pray | 71/94 |
| 4,011,062 A | | 3/1977 | Demchak et al. | 71/92 |
| 4,081,468 A | | 3/1978 | Baker et al. | 260/551 |
| 4,384,880 A | * | 5/1983 | Large | 71/87 |
| 4,389,238 A | * | 6/1983 | Kaufman | 71/117 |
| 4,405,531 A | | 9/1983 | Franz | 260/501.12 |
| 4,525,202 A | * | 6/1985 | Large et al. | 71/86 |
| 4,552,582 A | * | 11/1985 | Kruger | 71/73 |
| 4,783,342 A | | 11/1988 | Polovina | 427/4 |
| 4,806,275 A | | 2/1989 | Johnson et al. | 252/554 |
| 4,859,699 A | * | 8/1989 | Carney et al. | 514/447 |
| 5,658,853 A | * | 8/1997 | Kassebaum et al. | 504/206 |

FOREIGN PATENT DOCUMENTS

| | | | |
|---|---|---|---|
| EP | 220902 | * | 5/1987 |
| EP | 0220903 | | 5/1987 |
| EP | 0364202 | | 4/1990 |

OTHER PUBLICATIONS

*McCutcheon's Emulsifiers and Detergents*, 1990 North American Edition, McPublishing Co, Glen Rock NJ p. 177.*
Tedeschi, "Surfynol® Adjuvants—Greenhouse and Field Studies" (date unknown).
Air Products and Chemicals, Inc., "Surfynol® TG–E" ©1978, 1982.
Air Products and Chemicals, Inc., "Surfynol® 400 Series Surfactants" (date unknown).
Air Products and Chemicals, Inc., "Surfynol® Surfactants—Performance in Agricultural Chemicals", (1980).

* cited by examiner

*Primary Examiner*—S. Mark Clardy
(74) *Attorney, Agent, or Firm*—Howrey Simon Arnold & White, LLP; Patricia A. Kammerer; Ira D. Finkelstein

(57) ABSTRACT

A herbicide composition is provided comprising a glyphosate herbicide, an activity enhancing alkyl polyglycoside surfactant, and a foam moderating acetylenic diol.

5 Claims, 1 Drawing Sheet

HERBICIDAL COMPOSITIONS AND METHODS FOR PREPARING AND USING THE SAME

Figure 1:
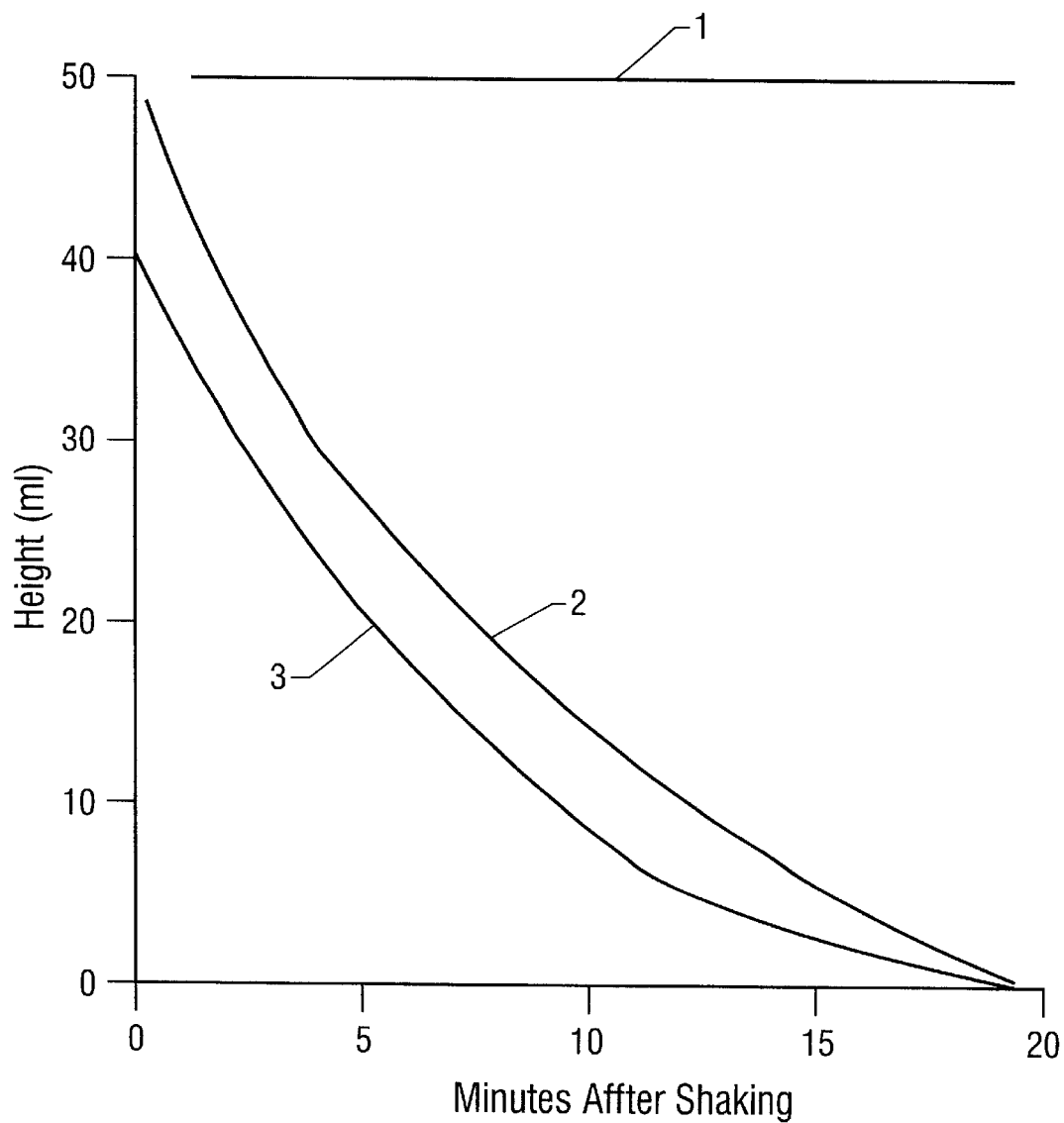

This application is a continuing application of application Ser. No. 07/739,945, filed Aug. 2, 1991, abandoned.

FIELD OF THE INVENTION

The present invention relates to new and useful herbicidal compositions of N-phosphonomethyl-glycine and/or an agriculturally acceptable salt thereof in aqueous solution containing certain herbicidal activity-enhancing nonionic surfactants and a class of foam moderators.

BACKGROUND OF THE INVENTION

N-Phosphonomethylglycine, also known by its common name glyphosate, and herbicidal salts thereof are highly effective and commercially important herbicides useful in controlling a wide variety of unwanted vegetation. The herbicide is normally applied to the foliage of a very broad spectrum of annual and perennial grasses, broadleaf plants and the like. Once within the plant, the herbicide translocates and is lethal to the whole plant. Usually, glyphosate is formulated in herbicidal compositions in the form of a selected water soluble salt. Commercially, glyphosate in the form of its monoisopropylamine salt is most often sold in concentrated aqueous solution which normally also contains an appreciable amount of a surfactant. The presence of a surfactant provides more efficient utilization of glyphosate and/or its salts dissolved in aqueous solution as compared to like glyphosate-containing solutions to which no surfactant has been added. The more efficient utilization of glyphosate and/or its salts occurs independently of whether the surfactant is anionic, cationic or nonionic.

An undesirable side-effect of the presence of surfactant can be the generation of foam, especially during dilution, mixing and spraying of the herbicide by the user. Alkyl polyglycosides are a class of surfactants useful for enhancing the herbicidal activity of glyphosate formulations but unfortunately have a strong tendency to generate foam which is slow to dissipate.

In European Patent Application 0 220 902 this drawback of alkyl pplyglycoside is not pointedly discussed, but it is suggested that an antifoam agent may be included when an alkyl polyglycoside surfactant is formulated with an aqueous solution of glyphosate. The only antifoam agent suggested in that patent is broadly described as a dimethylpolysiloxane. Most antifoam agents, such as the siloxanes, function by being in a separate phase from the aqueous solution, which allows the antifoam agent to rupture the film surrounding the entrapped air. Thus, in a spray solution, it is desirable that the antifoam agent be insoluble in the aqueous phase of the solution. However, this can have negative effects on the aqueous concentrate solution that is diluted to form the spray solution. It has been found that when silicones, such as the dimethylsiloxanes as suggested in the patent, are used as antifoam agents for aqueous concentrate solutions of glyphosate and an alkyl polyglycoside, a non-homogeneous formulation results upon standing over a relatively short period of time. In other words, there is a pronounced tendency of the silicone to separate from the aqueous concentrate solution as a separate layer. Thus, in such aqueous solutions, the silicone will have to be redispersed before pouring or drawing aliquots of the formulation from its container in order to realize the antifoam properties of the silicone in all aliquots. This redispersion requires agitation, for example, by shaking and stirring. A requirement for shaking or otherwise agitating agricultural chemical formulations prior to use is often ignored by the user, even when clearly advised on the label of the container. When large containers of aqueous concentrate solutions of glyphosate are used, accomplishing the needed agitation may be impractical impossible. Therefore, it is desired in the art to provide an aqueous concentrate formulation of glyphosate containing an alkyl polyglycoside surfactant having an antifoam agent such that the formulation is a homogeneous aqueous concentrate solution where the antifoam agent does not separate with time, yet shows good antifoam properties on dilution with water.

In a publication copyrighted in 1980 by Air Products and Chemicals, Inc. and entitled "Surfynol® Surfactants—Performance in Agricultural Chemicals", it is disclosed that such acetylenic diol surfactants provide beneficial effects in certain agricultural chemical formulations including wetting/surfactant potentiation, antifoam properties, compatibility with other adjuvants and anticorrosion properties. There is no disclosure of using the Surfynol surfactants to moderate the foam problems with aqueous solutions of glyphosate or with any agricultural chemical formulation containing an alkyl polyglycoside surfactant.

In normal agricultural applications, glyphosate is delivered from the herbicide manufacturer to the user in concentrated liquid form. For example, a commercial formulation may contain about 41% monoisopropylammonium glyphosate, as the herbicidally active ingredient, and about 15% surfactant with the remainder water. The glyphosate-containing aqueous solutions are applied at various rates using various application equipment and techniques. Spraying of diluted solutions of the herbicide on the target foliage is often accomplished with aerial broadcast spray, hand-held or boom-mounted applicators which produce a spray of desired force and configuration of active ingredient delivered at a predetermined rate. Spray solutions of the herbicidal compositions may contain from about one-half percent active ingredient to about five percent active ingredient or more to provide a delivery rate to the target plants of about 0.112 kilograms/hectare (kg/ha) to about 11.2 kg/ha. Thus, many commercial formulations of glyphosate and/or its salts require dilution with water. The formulated glyphosate and/or its herbicidal salts mix readily with water. The dilution may be accomplished by filling the mixing or spray tank with the required amount of water and adding the proper amount of formulated glyphosate or salts thereof. The resulting mixture requires agitation, for example, by circulation or agitation stirring. During mixing and application of the herbicidal composition, undesirable formation of foam of the spray solution may occur. While the above-mentioned alkyl polyglycoside surfactant facilitates the efficient use of the activity of the glyphosate and/or salts thereof dissolved in aqueous solution, the use of conventional application techniques is limited because of the foaming problems.

The present invention provides a stable, homogeneous, concentrate formulation of glyphosate and/or its salts, a herbicidally enhancing amount of an alkyl polyglycoside surfactant, and a foam moderating amount of a Surfynol surfactant, that does not foam unacceptably during dilution, mixing, or spraying. This concentrate formulation does not require shaking or stirring before being poured or drawn from the container in which it is supplied, such that each aliquot does not foam unacceptably during dilution, mixing, or spraying. There is no tendency of the Surfynol surfactant to separate from the solution as a separate layer. Upon dilution, the spray solution may be hazy, which indicates that the spray solution is non-homogeneous and at least two phases exist. This haziness is presumably the Surfynol surfactant, which is not soluble in the aqueous phase of the spray solution, which can then function as an antifoam agent in the spray solution. Thus, the glyphosate and/or its salts, alkyl polyglycoside surfactant, and Surfynol surfactant form a homogeneous aqueous concentrate solution, but the spray solution formed upon dilution of the aqueous concentrate solution is non-homogeneous.

SUMMARY OF THE INVENTION

There is provided a herbicidal composition comprising an aqueous concentrate homogeneous solution of a) glyphosate and/or a herbicidal salt thereof in concentrated form;

b) an activity enhancing amount of at least one alkyl polyglycoside surfactant; and c) a foam moderating amount of at least one acetylenic diol structurally characterized by a symmetrically substituted triple bond and adjacent hydroxyl groups.

Foaming which would normally occur when a diluted aqueous solution of glyphosate and/or its salts is agitated in the presence of an alkyl polyglycoside surfactant is moderated by the use of the composition of the present invention.

The composition in liquid form is prepared by mixing together a glyphosate herbicide, an activity enhancing alkyl polyglycoside surfactant, an acetylenic diol foam moderator, and water to form a homogeneous aqueous concentrate solution wherein the herbicide is present in an amount greater than required for vegetation control. Thereafter, the resulting concentrate solution may be diluted with additional water to adjust the glyphosate concentration to a suitable spray concentration. The resulting diluted solution may be hazy, thereby indicating non-homogeneity. The diluted solution has a reduced foam-forming propensity by comparison with a similar solution lacking the acetylenic diol. The foam more readily dissipates upon standing and forms in lesser amounts when the foam moderating diol is used in accordance with the present invention. The composition of the present invention may be formulated as a powder or granules in which case water will be added later.

REFERENCE TO DRAWING

The drawing depicts typical foam dissipation curves when an acetylenic diol foam moderator is used to control foam resulting from a vigorous agitation of an aqueous solution of glyphosate and/or its salts and an alkyl polyglycoside surfactant.

DETAILED DESCRIPTION

The present invention provides a herbicidal composition containing a herbicidally enhancing quantity of an alkyl polyglycoside and having present a foam controlling quantity of an acetylenic diol foam moderator.

The active herbicidal ingredient in the compositions of the present invention is N-phosphono-methylglycine whose common name is glyphosate. Glyphosate is an organic acid of limited water solu-bility. To enhance such solubility glyphosate is conventionally used in the form of one or more of its water soluble salts. One commercially available glyphosate-containing herbicide has as its active ingredient the isopropylamine salt of glyphosate. The concentration of the active ingredient is given in weight percent of isopropylamine salt of glyphosate; but in terms of activity, the concentration of glyphosate is better expressed in terms of acid equivalency (a.e.). For example, a composition containing 480 grams per liter of the active ingredient isopropylamine salt of N-phosphonomethylglycine is the equivalent of 356 grams per liter of the acid, glyphosate. While the isopropylamine salt of glyphosate is available commercially, any herbicidal salt of glyphosate is also useful in the compositions of the present invention.

In order to enhance the activity of the glyphosate-containing liquid compositions herein, a suitable alkyl polyglycoside surfactant is added together with water. For each part of glyphosate (a.e.), about 0.01 part to about 2 parts of the alkyl polyglycoside is used in formulating the compositions of the present invention. Preferably, the alkyl polyglycoside will be used in an amount of 0.2 to 1.0 part per part of glyphosate. The alkyl polyglycoside should be used in an amount sufficient to enhance the herbicidal activity of the glyphosate and/or its salts.

Suitable liquid alkyl polyglycoside surfactants useful in accordance with the present invention can be depicted by the following molecular structure

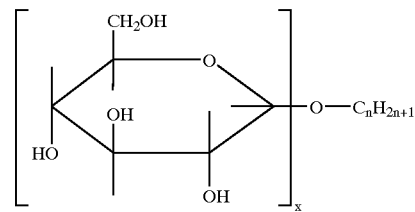

wherein n is an integer of about 8–18, preferably about 9–12 and x is 1 to about 8, preferably 1 to about 3 with an average value most preferably being about 1.2 to 1.8.

To control the foaming when glyphosate and/or its salts are agitated or vigorously mixed with the above-described alkyl polyglycoside surfactant in the presence of water, a foam controlling or moderating amount of at least one acetylenic diol as defined herein is used.

For each part glyphosate (a.e.), about 0.01 to about one part of the symmetrical acetylenic diol is used in formulating the compositions of the present invention. Preferably, the acetylenic diol will be used in an amount of 0.05 to 0.4 part per part of glyphosate.

The symmetrical tertiary acetylenic diols used as foam moderators in accordance with the present invention correspond to the following structural formula

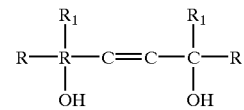

wherein R is hydrogen or a lower alkyl group, either branched or straight chains, containing 1 to about 8 carbon atoms, e.g., methyl, ethyl, propyl, isopropyl, n-butyl, isobutyl, pentyl, etc.; and where $R_1$ is a radical selected from the group consisting of methyl, ethyl, cyclopropyl and phenyl.

Representative compounds of suitable defoamers include:

2,5-dicyclopropyl-3-hexyne-2,5-diol, 3,6-diethyl-4-octyne-3,6-diol, 2,4,7,9-tetramethyl-5-decyne-4,7-diol, 4,7-dimethyl-5-decyne-4,7-diol, 2,3,6,7-tetramethyl-4-octyne-3,6-diol, 3,6-dimethyl-4-octyne-3,6-diol, 2,5-diphenyl-3-hexyne-2,5-diol,
2,5-dimethyl-3-hexyne-2,5-diol,
5,8-dimethyl-6-dodecyne-5,8-diol,
2,5,8,11-tetramethyl-6-dodecyne-5,8-diol, and the like.

It has been found that, most things considered, 2,4,7,9-tetramethyl-5-decyne-4,7-diol and 2,5,8,11-tetramethyl-6-dodecyne-5,8-diol are the preferred foam moderators.

It is sometimes advantageous to include in the herbicidal formulation a small amount of propylene glycol, dipropylene glycol or a like glycol solubilizer to more completely dissolve the diol in concentrated solution. When included, for each part of diol foam moderator, about 0.1 to 2 parts of propylene glycol are used for best results. Preferably, for each part of diol foam moderator, about 1.0 to 1.5 part of solubilizing glycol is used.

The compositions of the present invention are all homogeneous, transparent solutions. The foam moderating properties are realized upon dilution into a spray solution. The spray solution may be hazy, indicating non-homogeneity of the solution.

The following examples merely illustrate the practice of the present invention. Obviously, the invention is not limited thereto. In the examples all weights and percentages are given on a percent weight basis unless otherwise indicated.

EXAMPLE 1

In a container one part of the monoisopropylamine salt of glyphosate, 1.17 part water, and 0.27 part of the alkyl polyglycoside where x in the above structural formula was 1.6 and n is mostly in the 9–11 range were stirred together to form a homogeneous mixture.

EXAMPLE 2

In a container one part of the monoisopropylamine salt of glyphosate, 0.97 part of water, 0.27 part of the same alkyl polyglycoside that was used in Example 1, and 0.20 part of a 30% solution of 2,5,8,11-tetramethyl-6-dodecyne 5,8-diol in dipropylene glycol were stirred together to form a homogeneous mixture.

EXAMPLE 3

In a container one part of the monoisopropyl-amine salt of glyphosate, 0.78 part of water, 0.27 part of the same alkyl polyglycoside that was used in Example 1, and 0.24 part of a 50% solution of 2,4,7,9-tetramethyl-5-decyne-4,7-diol in propylene glycol, and 0.16 propylene glycol were stirred together to form a homogeneous mixture.

EXAMPLE 4

The composition of Example 1 was diluted with water to provide a spray solution containing 0.93% glyphosate a.e. The spray solution was clear. Fifty mls of the diluted solution was placed in a 100 ml graduate cylinder. The cylinder was stopped and vigorously shook over a period of fifteen seconds. After the shaking was stopped, it was noted that the foam completely filled the headspace of the cylinder. Even after 30 minutes the headspace was still filled with foam. In the drawing curve 1 illustrates the persistency and amount of the foam.

EXAMPLE 5

The composition of Example 2 was diluted with water to provide a spray solution containing 0.93% glyphosate. The spray solution was hazy. Fifty mls of the diluted solution was placed in a 100 ml graduate cylinder. The cylinder was stopped and vigorously shook over a period of fifteen seconds. It was noted that when the shaking was discontinued, the foam height in the graduate cylinder measured 50 ml. In a period of time of 10 minutes the foam height was measured to be 15 ml; and after 20 minutes substantially all of the foam had dissipated. In the drawing curve 2 illustrates the foam moderation due to the presence of the diol.

EXAMPLE 6

The composition of Example 3 was diluted with water to provide a spray solution containing 0.93% glyphosate. The spray solution was hazy. Fifty mls of the diluted solution was placed in a 100 ml graduate cylinder. The cylinder was stopped and vigorously shook over a period of fifteen seconds. It was noted that when the shaking was discontinued, the foam height in the graduate cylinder measured 40 ml. In a period of time of 10 minutes the foam height was only 10 ml; and after 20 minutes substantially all of the foam had dissipated. In the drawing curve 3 illustrates the foam moderation due to the presence of the diol.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A stable, homogeneous aqueous concentrated herbicidal composition comprising:

a) a glyphosate herbicide, the active ingredient of which is selected from an agriculturally acceptable salt of glyphosate or is glyphosate the acid, in a concentrated aqueous solution for postemergence controlling of weeds and grasses;

b) a glyphosate herbicide enhancing amount of alkyl polyglycoside having the structurally formula

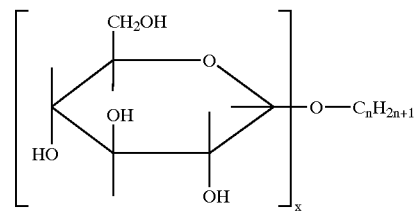

wherein x is 1 to about 8 and n is about 8–18; and c) a foam moderating amount of an acetylenic diol having the structural formula

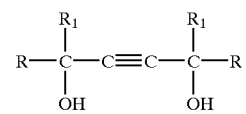

where R is an alkyl group either branched or straight chain containing 1 to about 8 carbon atoms and $R_1$ is a radical selected from the group consisting of methyl, ethyl, cyclopropyl and phenyl, said acetylenic diol added in an amount of about 0.01 to about 1.0 part per part of glyphosate.

2. The herbicidal composition of claim 1 wherein x is about 1.2 to 1.8.

3. The herbicidal composition of claim 1 wherein the salt is sodium, ammonium, trimethylsulfonium or the isopropylammonium salt.

4. A stable, homogeneous aqueous concentrated herbicidal composition comprising:

a) a glyphosate herbicide, the active ingredient of which is selected from an agriculturally acceptable salt of glyphosate or is glyphosate the acid, in a concentrated aqueous solution for postemergence controlling of weeds and grasses;

b) a glyphosate herbicide enhancing amount of an alkyl polyglycoside having the structural formula

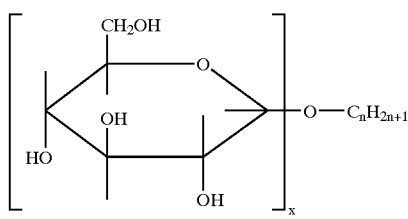

wherein x is 1 to about 8 and n is about 8–18; and c) a foam moderating amount of 2,4,7,9-tetramethyl-5-decyne- 4,7-diol, 2,5,8,11-tetramethyl-6-dodecyne-5,8-diol or mixture thereof, said acetylenic diol added in an amount of about 0.01 to about 1.0 part per part of glythosate.

5. A stable, homogeneous aqueous conscentrated herbicide composition conrising;

a) the isopropylmine salt of glyphosate, in concentrated queous solution;

b) a glyphosate hericide enhancing amount of an alkylpolyglycoside having the structural formula

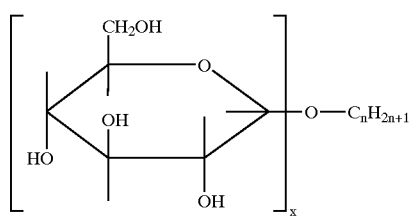

wherein x is about 1.6 on the average and n is in the range of about 9 to about 12, and c) a foam moderating amount of 2,4,7,9-tetramethyl-5 decyne-4,7-diol, 2,5,8,11-tetamathyl-6-dodecyne-5,8-diol, or mixture thereof, said acetylenic deiol added in an amount of about 0.01 to about 1.0 party per part of glyphosatae.

* * * * *

UNITED STATES PATENT AND TRADEMARK OFFICE
CERTIFICATE OF CORRECTION

PATENT NO.     : 6,500,782 B1                                           Page 1 of 1
DATED          : December 31, 2002
INVENTOR(S)    : James W. Kassebaum It is certified that error appears in the above-identified patent and that said Letters Patent is hereby corrected as shown below:

<u>Column 8,</u>
Line 3, replace "glythosate" with -- glyphosate --.
Line 4, replace "conscentrated" with -- concentrated --.
Line 5, replace "conrising" with -- comprising --.
Line 7, replace "queous" with -- aqueous --.
Line 8, replace "hericide" with -- herbicide --.
Lines 25 and 26, replace "2,4,7,9-tetramethyl-5 decyne-4,7-diol" with
-- 2,4,7,9-tetramethyl-5-decyne-4,7-diol --.
Lines 26 and 27, replace 2,5,8,11-tetamathyl-6-dodecyne-5,8-diol," with
-- 2,5,8,11-tetramethyl-6-dodecyne-5,8-diol --.
Line 27, replace "deiol" with -- diol --.
Line 28, replace "party" with -- part --.
Line 29, replace "glyphosatae" with -- glyphosate --.

Signed and Sealed this

Fifteenth Day of April, 2003

JAMES E. ROGAN
*Director of the United States Patent and Trademark Office*